(12) United States Patent
Krupica et al.

(10) Patent No.: US 9,713,238 B2
(45) Date of Patent: Jul. 18, 2017

(54) ROTATING MEMBER FOR RADIATION IMAGING MODALITY CONFIGURED TO FACILITATE CONTACTLESS TRANSFER OF INFORMATION AND/OR POWER AND/OR TO FACILITATE ASCERTAINING ROTATION ANGLE OF ROTATING MEMBER

(75) Inventors: Libor Krupica, Nashua, NH (US); John Hickey, Merrimack, NH (US); Chris Hardy, Hampton, NH (US)

(73) Assignee: Analogic Corporation, Peabody, MA (US)

( * ) Notice: Subject to any disclaimer, the term of this patent is extended or adjusted under 35 U.S.C. 154(b) by 613 days.

(21) Appl. No.: 13/534,635

(22) Filed: Jun. 27, 2012

(65) Prior Publication Data

US 2014/0003583 A1 Jan. 2, 2014

(51) Int. Cl.
*A61B 6/00* (2006.01)
*H05G 1/10* (2006.01)
*A61B 6/03* (2006.01)

(52) U.S. Cl.
CPC .............. *H05G 1/10* (2013.01); *A61B 6/032* (2013.01); *A61B 6/56* (2013.01)

(58) Field of Classification Search
CPC ........................................................ A61B 6/56
See application file for complete search history.

(56) References Cited

U.S. PATENT DOCUMENTS

| | | | | |
|---|---|---|---|---|
| 4,173,762 A | * | 11/1979 | Thompson et al. | 343/759 |
| 4,916,718 A | * | 4/1990 | Manring | 378/4 |
| 5,577,026 A | * | 11/1996 | Gordon et al. | 370/278 |
| 5,608,771 A | * | 3/1997 | Steigerwald et al. | 378/15 |
| 5,978,438 A | * | 11/1999 | Resnick et al. | 378/4 |
| 6,368,049 B1 | * | 4/2002 | Osaka et al. | 414/783 |
| 6,387,327 B1 | * | 5/2002 | Ricci et al. | 422/72 |
| 6,388,257 B1 | * | 5/2002 | Gagnon et al. | 250/363.04 |
| 7,899,150 B2 | * | 3/2011 | Beyerlein et al. | 378/15 |
| 2007/0035883 A1 | * | 2/2007 | Katcha et al. | 360/281.8 |
| 2007/0188284 A1 | * | 8/2007 | Dobbs | 336/120 |
| 2007/0195924 A1 | * | 8/2007 | Krumme | 378/15 |
| 2010/0066340 A1 | * | 3/2010 | Delforge | A61B 6/56 323/305 |
| 2012/0262001 A1 | * | 10/2012 | Friesner | A61B 6/032 307/104 |

* cited by examiner

*Primary Examiner* — Dani Fox
(74) *Attorney, Agent, or Firm* — Cooper Legal Group, LLC

(57) ABSTRACT

Among other things, one or more rotating members of a radiation imaging modality, such as a CT system, are described herein. The rotating member may be configured to support at least one of a radiation source or a detector array and comprises at least one element configured to facilitate the transfer of power to the rotating member and at least one element configured to facilitate the transfer of information between the rotating member and a stator. The rotating member may also comprise one or more positioning elements that are formed within the rotating member and are configured to facilitate determining a rotation angle of the rotating member. The rotating member may further comprise, among other things, a bearing structure, antenna assembly for transferring image data, and/or a drive mechanism for facilitating rotation of the rotating member, for example.

20 Claims, 7 Drawing Sheets

ROTATING MEMBER FOR RADIATION IMAGING MODALITY CONFIGURED TO FACILITATE CONTACTLESS TRANSFER OF INFORMATION AND/OR POWER AND/OR TO FACILITATE ASCERTAINING ROTATION ANGLE OF ROTATING MEMBER

BACKGROUND

The present application relates to a rotating member (e.g., rotating gantry) of a radiation imaging modality. It finds particular application in the context of computed tomography imaging modalities, where power and information (e.g., image data, communication data, gate drive signals, etc.) are transferred through an airgap that separates the rotating member from a stator. More particularly, the instant application relates to the contactless transfer of such power and information.

Computed tomography (CT) imaging modalities are configured to generate volumetric data corresponding to an object under examination. In this way, images may be generated that allow personnel to identify security threats, determine the orientation/position of a tumor in a body, etc. To generate such data, the computed tomography imaging modality is typically configured to rotate a radiation source and detector array about the object under examination (e.g., causing the object to be viewed from a plurality of angles). For example, the radiation source and/or detector array may be mounted to a rotating member (e.g., a rotating gantry, such as a rotating disk, rotating drum, etc.) configured for rotation relative to a stator (e.g., a stationary member) configured to support the rotating member.

When an object is to be examined, the object is positioned in a bore of the rotating member (e.g., between the radiation source and the detector array) and radiation is emitted. Based upon the amount of radiation absorbed and/or attenuated by the object, one or more images of the object may be formed. For example, highly dense aspects of the object typically absorb and/or attenuate more radiation than less dense aspects, and thus an aspect having a higher density, such as a bone or metal, for example, may be apparent in an image when surrounded by less dense aspects, such as muscle or clothing.

Given that the radiation source and detector array are mounted on the rotating member, power and information (e.g., instructing the radiation source and/or other electronic components how to operate) are typically supplied to the rotating member from the stator. Moreover, imaging data (e.g., data generated in response to the detection of radiation by the detector array) and/or other communication/status information is typically transferred from the rotating member to the stator (e.g., for further processing and/or to be displayed to security/medical personnel).

Conventionally, slip-ring assemblies have been used to transfer power and/or information (e.g., control information, communication information, and/or imaging data) between the stator and the rotating member. Slip-ring assemblies are typically configured to transfer power and/or information between a stator and a movable member (e.g., a rotating member) and/or between two movable members through the physical contact of two materials (e.g., via a sliding contact). For example, a slip-ring attached to the stator may comprise metal brushes that are configured to physically contact an electrically conductive surface of a slip-ring attached to the movable member, allowing power and/or information to be transferred between the stator and the movable member.

While the use of slip-ring assemblies has proven effective for transferring power and/or information between a stator and a movable unit (e.g., a rotating member) and/or between two movable units, conventional slip-ring assemblies may generate dust or particles (e.g., as metal brushes wear down), may be unreliable (e.g., again as contact surfaces, such as metal brushes, wear), and/or may be noisy (e.g., as surfaces rub against one another), which may cause interference with some procedures (e.g., CT imaging). Other drawbacks of slip-ring assemblies may include cost and complexity of manufacture due to special materials and/or mechanical precision that may be required.

SUMMARY

Aspects of the present application address the above matters, and others. According to one aspect, a rotating member of a radiation imaging modality is provided. The rotating member comprises at least first and second channels disposed on a same surface of the rotating member and an electrically conductive first element configured to facilitate power transfer between the rotating member and a stator of the radiation imaging modality, the first element comprised within the first channel. The rotating member also comprises a ferromagnetic material disposed between the first element and a surface of the first channel and an electromagnetic second element configured to facilitate information transfer between the rotating member and the stator. The second element is comprised within the second channel.

According to another aspect, a rotating member for a computed tomography (CT) imaging modality is provided. The rotating member is configured to support at least one of a radiation source or a detector array and comprises one or more positioning elements that are formed within the rotating member and are configured to facilitate ascertaining a rotation angle of the rotating member.

According to another aspect, a computed tomography (CT) imaging modality comprising a stator and a rotating member is provided. The rotating member comprises at least first and second channels disposed on a same surface of the rotating member and an electrically conductive first element configured to facilitate power transfer between the rotating member and the stator, the first element comprised within the first channel. The rotating member also comprises a ferromagnetic material disposed between the first element and a surface of the first channel and an electromagnetic second element configured to facilitate information transfer between the rotating member and the stator. The second element is comprised within the second channel. The stator comprises at least third and fourth channels disposed on a same surface of the stator and an electrically conductive third element configured to facilitate power transfer between the rotating member and the stator, the third element comprised within the third channel. The stator also comprises a ferromagnetic material disposed between the third element and a surface of the third channel and an electromagnetic fourth element configured to facilitate information transfer between the rotating member and the stator. The fourth element is comprised within the fourth channel. The third channel faces the first channel and the fourth channel faces the second channel. The first and second channels are respectively separated from the third and fourth channels via an airgap.

Those of ordinary skill in the art may appreciate still other aspects of the present application upon reading and understanding the appended description.

FIGURES

The application is illustrated by way of example and not limitation in the figures of the accompanying drawings, in which like references indicate similar elements and in which.

DESCRIPTION

Figure 1:
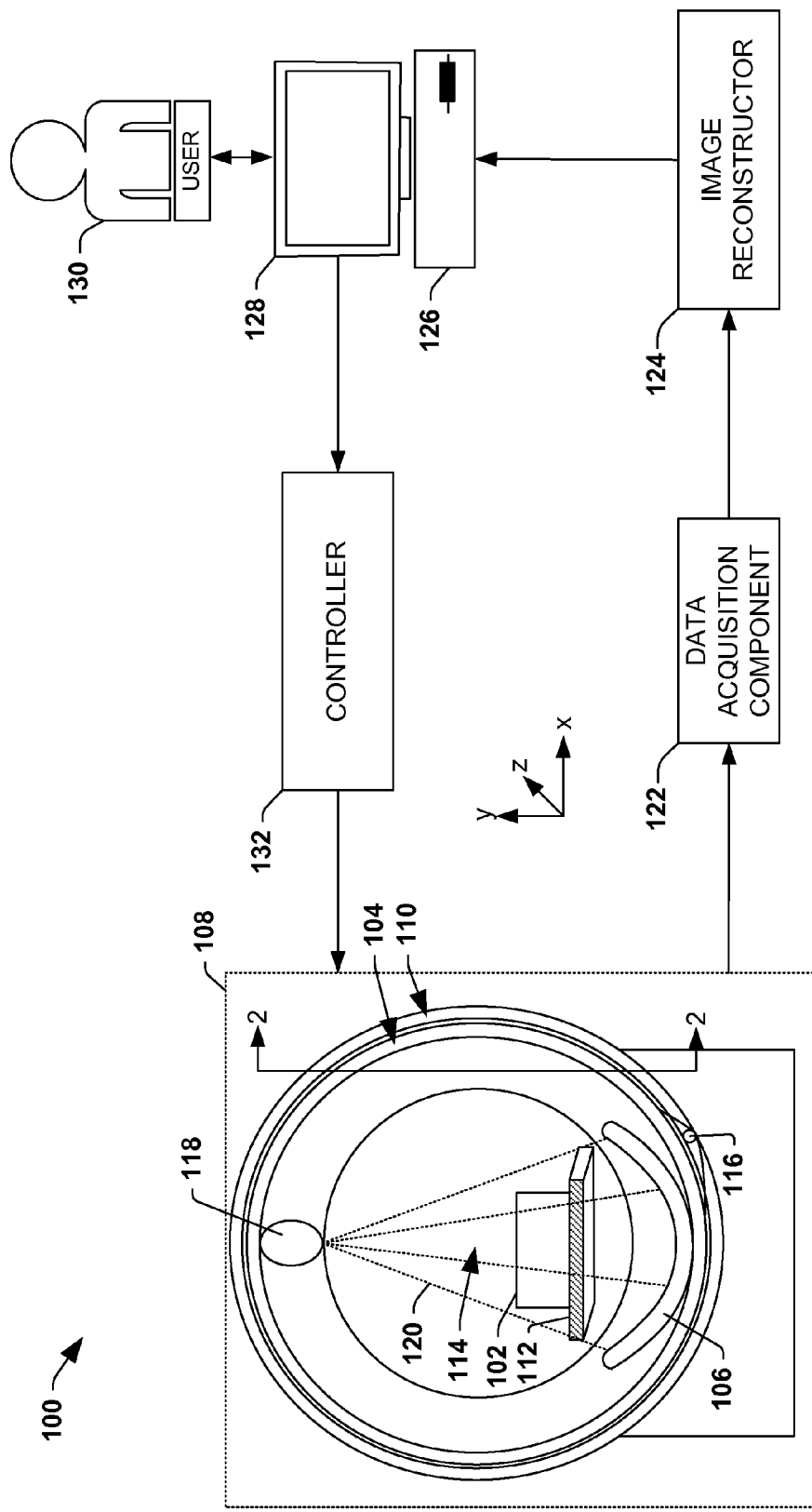
FIG. 1 illustrates a block diagram of an example radiation imaging modality.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

The present disclosure relates to a rotating member of an imaging modality, such as a computed tomography (CT) system, machined or manufactured to provide for numerous functions (e.g., to improve manufacturing accuracy, reduce manufacturing time, and/or reduce a number of components attached to the rotating member relative to conventional CT imaging modalities, etc.). By way of example, the rotating member may be machined with a plurality of channels and material may be inserted into respective channels to provide functionality of the rotating member (e.g., apart from its general function of a support for a radiation source and/or detector array). For example, electrically conductive material configured to facilitate the contactless transfer of high voltage power and/or auxiliary power to the radiation source and/or other electronic components attached to the rotating member may be comprised within one or more channels. Electromagnetic material configured to facilitate the contactless transfer of information (e.g., control information, communication information, etc.) between a stator and the rotating member may be comprised within one or more other channels. A drive mechanism (e.g., such as a belt, rope, etc.) may be comprised within yet another channel. Moreover, the rotating member may be machined/manufactured to comprise one or more positioning elements, which may be utilized to facilitate ascertaining a rotation angle of the rotating member, for example. Further, the rotating member may comprise an antenna for transferring image data between the rotating member and the stator and/or the rotating member may comprise a surface for attaching such an antenna. The rotating member may also be machined/manufactured with a bearing surface (or bearing face), such that the rotating member may be part of a bearing that provides for rotating the rotating member.

Note that "noncontact," "contactless," and/or the like is used herein to refer to the ability to transfer information in inductive fashion between or among bodies configured for relative movement, and should not be understood to necessarily preclude possible contact between or among such bodies for other purposes, including, for example, electrostatic discharge, exchange or transmission of data, mechanical drive or support, braking and safety mechanisms, low-voltage power transfer, and/or high-voltage power transfer, etc.

It should also be noted that in the present disclosure, except where otherwise clear from context, "gap" and "airgap" are used more or less interchangeably; although "airgap" may be used herein, as this should be understood to be mere deference to convention, it should be understood that such gaps are not limited to air, it being possible for vacuum, oil, and/or other fluid and/or gas, and/or sliding and/or roller bearings or other such contrivances permitting relative movement to completely or partially fill such spaces.

FIG. 1 is an illustration of an example environment 100 where a rotating member 104 supporting one or more of the foregoing features, among other features, may be useful. More particularly FIG. 1 illustrates an example computed tomography (CT) system that can be configured to acquire volumetric information regarding an object 102 under examination and generate images therefrom.

It may be appreciated that while a CT system is described herein, the instant application is not intended to be so limited. That is, to the extent practical, the instant application, including the scope of the claimed subject matter, is intended to be applicable to other imaging modalities that comprise a movable member (e.g., a rotor or rotating member) and a stationary member (e.g., a stator) and/or two movable members. Moreover, the example environment 100 merely illustrates an example schematic and is not intended to be interpreted in a limiting manner, such as necessarily specifying the location, inclusion, and/or relative arrangement of the components described herein. For example, the data acquisition component 122 may be mounted to the rotating member 104 portion of an object examination apparatus 108, or more particularly may be part of a detector array 106, for example.

In the example environment 100, the object examination apparatus 108 is configured to examine one or more objects 102 (e.g., a series of suitcases at an airport, a human patient, etc.). The object examination apparatus 108 can comprise a rotating member 104 and a stator 110 (e.g., also referred to herein as a stationary member) configured to, among other things, support the rotating member. During an examination of the object(s) 102, the object(s) 102 can be placed on a support article 112, such as a bed or conveyor belt, that is selectively positioned in an examination region 114 (e.g., a hollow bore in the rotating member 104), and the rotating member 104 can be rotated about the object(s) 102 by a rotator 116 (e.g., motor, drive shaft, chain, etc.).

The rotating member 104 may surround a portion of the examination region 114 and may support one or more radiation sources 118 (e.g., an ionizing x-ray source) and a detector array 106 that is mounted on a substantially diametrically opposite side of the rotating member 104 relative to the radiation source(s) 118. As will be described in more detail below, power and/or communication information supplied to components physically coupled to the rotating member 104 such as the radiation source 118 and/or detector array 106 may be transferred via contactless elements comprised within channels of the rotating member 104 (and similarly designed contactless elements comprised within channels of the stator 110). Moreover, in one embodiment, a rotation angle of the rotating member 104 (e.g., defining a number of degrees that the rotating member 104 has rotated relative to a reference) may be determined based at least in part upon a positioning element at least partially formed within the rotating member 104 and/or other positional aspects of the rotating member 104. Further, the rotating member 104 may comprise an antenna for transferring image data from the detector array 106 to the data acquisition component 122 and/or image reconstructor 124 (e.g., positioned on a stationary side of the CT imaging modality). It may be appreciated that at least some of these and other features of the rotating member 104 may be described in further detail below.

During an examination of the object(s) 102, the radiation source(s) 118 emits fan, cone, wedge, and/or other shaped radiation 120 configurations into the examination region 114 of the object examination apparatus 108. It may be appreciated that such radiation may be emitted substantially continuously and/or may be emitted intermittently (e.g., a short pulse of radiation is emitted followed by a resting period during which the source is not activated).

As the emitted radiation 120 traverses the object(s) 102, the radiation 120 may be attenuated differently by different aspects of the object(s) 102. Because different aspects attenuate different percentages of the radiation 120, an image(s) may be generated based upon the attenuation, or variations in the number of radiation photons that are detected by the detector array 106. For example, more dense aspects of the object(s) 102, such as a bone or metal plate, may attenuate more of the radiation 120 (e.g., causing fewer photons to be detected by the detector array 106) than less dense aspects, such as skin or clothing.

The detector array 106 is configured to directly convert (e.g., using amorphous selenium and/or other direct conversion materials) and/or indirectly convert (e.g., using photodetectors and/or other indirect conversion materials) detected radiation into signals that can be transmitted from the detector array 106 to a data acquisition component 122 configured to compile signals that were transmitted within a predetermined time interval, or measurement interval, using various techniques (e.g., integration, photon counting, etc.). It may be appreciated that such a measurement interval may be referred to as a "view" and generally reflects signals generated from radiation 120 that was emitted while the radiation source 118 was at a particular angular range relative to the object 102. Based upon the compiled signals, the data acquisition component 122 can generate projection data indicative of the compiled signals, for example.

The example environment 100 further comprises an image reconstructor 124 configured to receive the projection data that is output by the data acquisition component 122. The image reconstructor 124 is configured to generate image data from the projection data using a suitable analytical, iterative, and/or other reconstruction technique (e.g., back-projection reconstruction, tomosynthesis reconstruction, iterative reconstruction, etc.). In this way, the data is converted from projection space to image space, a domain that may be more understandable by a user 130 viewing the image(s), for example.

The example environment 100 also includes a terminal 126, or workstation (e.g., a computer), configured to receive the image(s), which can be displayed on a monitor 128 to the user 130 (e.g., security personnel, medical personnel, etc.). In this way, a user 130 can inspect the image(s) to identify areas of interest within the object(s) 102. The terminal 126 can also be configured to receive user input which can direct operations of the object examination apparatus 108 (e.g., a speed to rotate, a speed of a conveyor belt, etc.).

In the example environment 100, a controller 132 is operably coupled to the terminal 126. In one example, the controller 132 is configured to receive input from the terminal 126, such as user input for example, and to generate instructions for the object examination apparatus 108 indicative of operations to be performed. For example, the user 130 may desire to reexamine the object(s) 102 at a different energy level, and the controller 132 may issue a command instructing the support article 112 to reverse direction (e.g., bringing the object(s) 102 back into an examination region 114 of the object examination apparatus 102) and instructing a power supply located on the rotating member 104 to increase a voltage applied to the radiation source 118 (e.g., causing the radiation output therefrom to have a higher energy).

As will be described in more detail below, power, commands, and/or other information that is transmitted between components physically attached to the rotating member 104 (e.g., such as the radiation source 118 and/or detector array 106) and substantially stationary components (e.g., such as the stator 110, controller 132, etc.) may be transmitted through an air-gap. In this way, few if any brushes may contact the rotating member 104 to reduce noise caused by the brushes and/or to reduce dust that may be created as the brushes wear down, for example.

Figure 2:
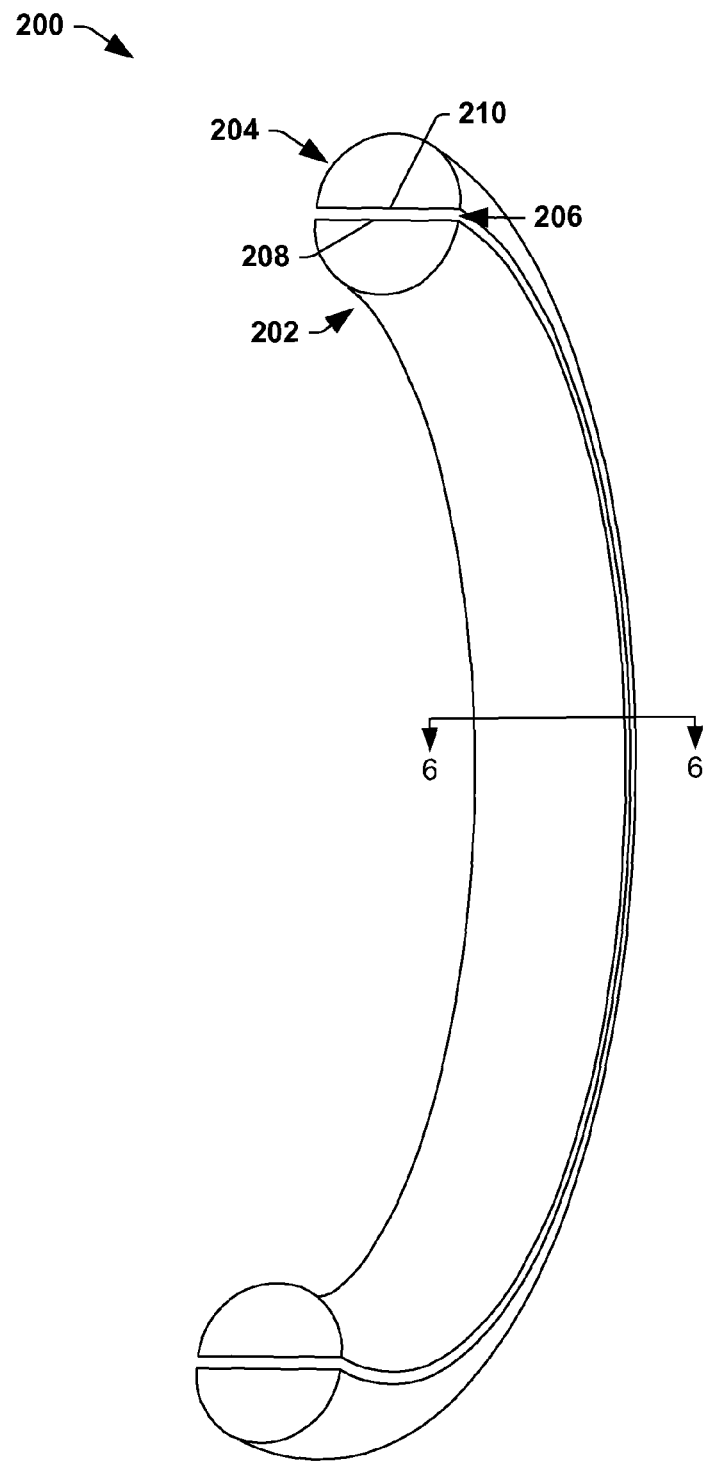
FIG. 2 illustrates an example arrangement of a rotating member and a stator separated by a cylindrical airgap.

FIG. 2 illustrates a cross-sectional view (e.g., taken along line 2-2 in FIG. 1) of an example arrangement 200 of a substantially annular-shaped rotating member 202 (e.g., 104 in FIG. 1) and a substantially annular-shaped stator 204 (e.g., 110 in FIG. 1). Respective members 202, 204 may be constructed of aluminum, steel, and/or other materials that provide sufficient tensile strength to support the load being applied thereto. By way of example, a radiation source and/or a detector array may be affixed to (e.g., cantilevered off of) the rotating member 202, and thus the rotating member 202 may be comprised of a material that is supportive of such a load. As yet another example, the rotating member 202 may be coupled to the stator 204 via a bearing structure (not shown), for example, and thus the stator 204 may be constructed to support the load applied by the rotating member 202. Further, as described above, during an examination of an object, the rotating member 202 may be rotated about an axis of rotation of the CT system or other imaging modality while the stator 204 may remain substantially fixed.

The rotating member 202 and the stator 204 are separated by a cylindrical airgap 206, where the cylindrical airgap does not relate to the cross-sectional view of the airgap (e.g., where such a cross-sectional view of the airgap has a substantially rectangular shape in FIG. 2), but instead relates to the entirety of the airgap between the annular rotating member 202 and the annular stator 204 (where less than all of the annular rotating member 202 and the annular stator 204 are illustrated in FIG. 2 (e.g., about a third of each are shown) and thus less than all of the cylindrical airgap (e.g., about a third) is illustrated in FIG. 2). That is, stated differently, the airgap 206 is situated between a radial surface 208 of the rotating member 202 and a radial surface 210 of the stator 202 (e.g., such that a line drawn through that airgap 206 (e.g., in a z-direction, substantially left to right on the page) would be substantially parallel to an axis of rotation). As will be described with respect to FIG. 6, when the airgap 206 is a cylindrically shaped airgap (as shown in FIG. 2), the radial surface 208 of the rotating member 202 and the radial surface 210 of the stator 204 may comprise channels (not shown) into which one or more electrically conductive elements and/or electromagnetic elements may be inserted. Power and/or information may be transmitted between the rotating member 202 and the stator 204 through the airgap 206 via these electrically conductive elements and/or electromagnetic elements. Moreover, as will be described in more detail with respect to FIGS. 4-6, the rotating member 202 and/or the stator 204 may be machined and/or manufactured to provide additional functionality to reduce a number of assemblies that are attached to the rotating member 202 and/or to provide for improved weight distribution of the rotating member 202 (e.g., relative to conventional rotating gantries of a CT system), for example.

It may be appreciated that in the illustrated embodiment, the rotating member 202 has a smaller diameter than the stator 204 (such that the ring formed by the rotating member 202 fits inside the ring formed by the stator 204). In another embodiment, the rotating member 202 may have a larger diameter than the stator 204 and may partially surround or encase the stator 204, for example.

Further, although FIG. 2 illustrates the rotating member 202 and the stator 204 as forming half-circles, it may be appreciated that other shaped structures are also contemplated and the rotating member 202 may be shaped differently than the stator 204. For example, in another embodiment, cross-sections of the rotating member 202 and/or stator 204 may be rectangular, as opposed to shaped as half-circles. Moreover, it may be appreciated that while the example environment 200 illustrates the rotating member 202 and the stator 204 as being substantially equal in width (e.g., when the radial surfaces 208, 210 are measured at the airgap 206), it may be appreciated that the rotating member 202 may be wider than the stator 204 and/or the stator 204 may be wider than the rotating member 202.

Figure 3:
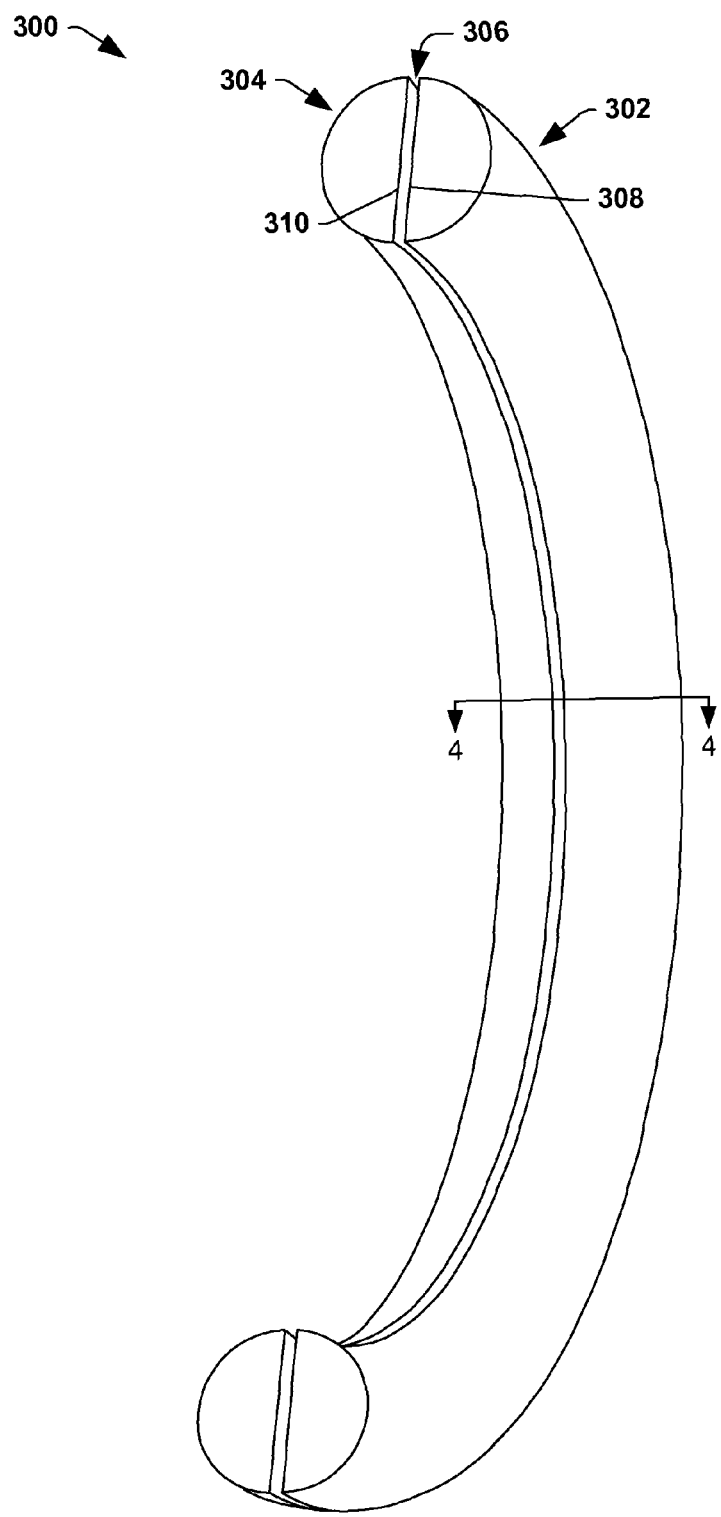
FIG. 3 illustrates an example arrangement of a rotating member and a stator separated by a planar airgap.

FIG. 3 illustrates a cross-sectional view of an example arrangement 300 of a substantially annular-shaped rotating member 302 (e.g., 104 in FIG. 1) and a substantially annular-shaped stator 304 (e.g., 110 in FIG. 1). In this example arrangement 300, the rotating member 302 and the stator 304 are separated by a planar airgap 306 (e.g., as opposed to a cylindrical airgap 206 as illustrated in FIG. 2). That is, stated differently, the airgap 306 is situated between an axial surface 308 of the rotating member 302 and an axial surface 310 of the stator 302 (e.g., such that a line drawn through the airgap 306 (e.g., substantially top to bottom on the page) would be substantially perpendicular to an axis of rotation). As with FIG. 2, the planar airgap does not relate to the cross-sectional view of the airgap (e.g., where such a cross-sectional view of the airgap has a substantially rectangular shape in FIG. 3), but instead relates to the entirety of the airgap between the annular rotating member 302 and the annular stator 304 (where less than all of the annular rotating member 302 and the annular stator 304 are illustrated in FIG. 3 (e.g., about a third of each are shown) and thus less than all of the planar airgap (e.g., about a third) is illustrated in FIG. 3.

As will be described with respect to FIGS. 4-5, when the airgap 306 is a planar airgap (as shown in FIG. 3), the axial surface 308 of the rotating member 302 and the axial surface 310 of the stator 304 may comprise one or more channels (not shown) into which one or more electrically conductive elements and/or electromagnetic elements may be inserted. Power and/or information may be transmitted between the rotating member 302 and the stator 304 through the airgap 306 via these electrically conductive elements and/or electromagnetic elements. Moreover, as will be described in more detail with respect to FIGS. 4-6, the rotating member 302 and/or the stator 304 may be machined and/or manufactured to provided additional functionality to reduce a number of assemblies that are attached to the rotating member 302 and/or to provide for improved weight distribution of the rotating member 302 (e.g., relative to conventional rotating gantries of a CT system), for example.

Although FIG. 3 illustrates the rotating member 302 and the stator 304 as forming half-circles, it may be appreciated that other shaped structures are also contemplated, and the rotating member 302 may be shaped differently than the stator 304. For example, in another embodiment, cross-sections of the rotating member 302 and/or stator 304 may be rectangular, as opposed to shaped as half-circles. Moreover, it may be appreciated that while the example environment 300 illustrates the rotating member 302 and the stator 304 as being substantially equal in length (e.g., when the axial surfaces 308, 310 are measured at the airgap 306), it may be appreciated that the rotating member 302 may have a greater length than the stator 304 and/or the stator 304 may be have a greater length than the rotating member 302. That is, axial surface 308 or 310 may extend past (e.g., be wider, taller, etc.) axial surface 310 or 308, respectively, for example.

Figure 4:
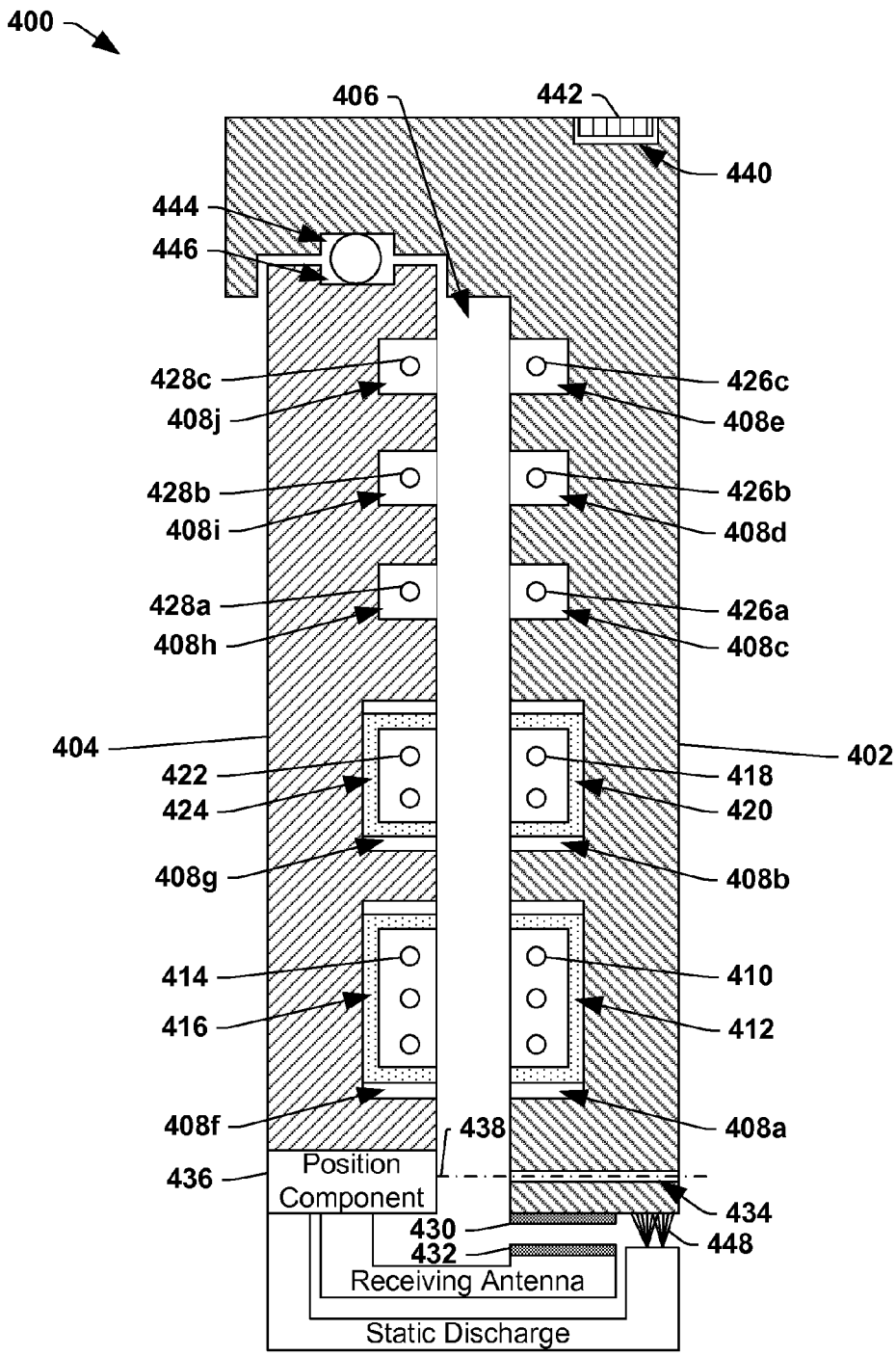
FIG. 4 illustrates a cross-sectional view of an example rotating member and a stator comprising elements to facilitate the transfer of power and/or information between the rotating member and the stator.

FIG. 4 illustrates a cross-sectional view 400 (e.g., taken along line 4-4 in FIG. 3) of an example rotating member 402 (e.g., 302 in FIG. 3) and a stator 404 (e.g., 304 in FIG. 3) separated by an airgap 406 (e.g., 306 in FIG. 3). The rotating member 402 comprises one or more channels 408a-e disposed on an axial surface (e.g., 308 in FIG. 3) and the stator 404 comprises one or more channels 408f-j disposed on an axial surface (e.g., 310 in FIG. 3) into which electrically conductive elements (e.g., solid or braided wires) and/or electromagnetic elements (e.g., electrically conductive elements, optical fibers, radio frequency chips, etc.) may be disposed to provide for contactless transfer of power and/or information across a (planar) airgap 406. In this way, information and/or power may be inductively transferred across the airgap 406, as opposed to using slip-rings to transfer such information/power, for example.

To facilitate the transfer of high voltage power between the rotating member 402 and the stator 404 (e.g., to supply a radiation source with high voltage power), the rotating member 402 may comprise an electrically conductive (annular shaped) first element 410 and a ferromagnetic material 412 (e.g., manganese-zinc, nickel-zinc, etc.). The first element 410 is comprised within a first channel 408a and the ferromagnetic material 412 is disposed between the first element 410 and a surface of the first channel 408a. The stator 404 may comprise an electrically conductive (annular shaped) first element 414 and a ferromagnetic material 416 respectively comprised within a first channel 408f of the stator 404, with the ferromagnetic material 416 disposed between the first element 414 and a surface of the first channel 408f. Together, these elements of the rotating member 402 and the stator 404 may form a transformer, where the first element 414 of the stator 404 may behave as a primary winding and the first element 410 of the rotating member 402 may behave as a secondary winding. Thus, the first element 410 of the rotating member 402 may be configured to inductively generate high voltage power via electro-magnetic fields produced by current flowing through the first element 414 of the stator 404. U.S. patent application Ser. No. 11/699,529 and PCT application PCT/US11/38777, both entitled "Shielded Power Coupling Device" and assigned to Analogic Corporation further describe example contactless power transfer systems that are configured to inductively transfer power between a stator and a rotating member that are separated by an airgap and are incorporated herein by reference.

It may be appreciated that in the illustrated embodiment, the first element 410 of the rotating member 402 and the first element 414 of the stator 404 respectively comprise three turns (e.g., the wire is looped in respective channels 408a, 408f three times). However, in other embodiments, the first element 410 and/or the first element 414 may comprise more turns or a fewer number of turns than the illustrated number of turns. Moreover, the number of turns in the first element 414 of the stator 404 may be different than the number of turns in the first element 410 of the rotating member 402 (e.g., so that voltage transformation occurs between the primary and secondary windings).

To facilitate the transfer of lower voltage (auxiliary) power between the rotating member 402 and the stator 404 (e.g., to provide power to components attached to the rotating member 402), the rotating member 402 may comprise an electrically conductive (annular shaped) second element 418 and a ferromagnetic material 420 (e.g., manganese-zinc, nickel-zinc, etc.). The second element 418 may be comprised within a second channel 408b and the ferromagnetic material 420 may be disposed between the second element 418 and a surface of the second channel 408b. The stator 404 may comprise an electrically conductive (annular shaped) second element 422 and a ferromagnetic material 424 respectively comprised within a second channel 408g of the stator 404, with the ferromagnetic material 424 disposed between the second element 422 and a surface of the second channel 408g. Together, these elements of the rotating member 402 and the stator 404 may form a transformer, where the second element 422 of the stator 404 may behave as a primary winding and the second element 418 of the rotating member 402 may behave as a secondary winding. Thus, the second element 418 of the rotating member 402 may be configured to inductively generate lower voltage power via electro-magnetic fields produced by current flowing through the second element 422 of the stator 404.

Although the second element 418 of the rotating member 402 and the second element 422 of the stator 404 respectively comprise two turns, in other embodiments the second element 418 and/or the second element 422 may comprise more turns or a fewer number of turns than the illustrated number of turns. Moreover, the number of turns in the second element 422 of the stator 404 may be different than the number of turns in the second element 418 of the rotating member 402 (e.g., so that voltage transformation occurs between the primary and secondary windings).

To facilitate information (e.g., communication information, commands, etc.) transfer between the rotating member 402 and the stator 404, the rotating member 402 may also comprise one or more electromagnetic elements 426a-c respectively comprised within a channel 408c-e and/or the stator 404 may comprise one or more electromagnetic elements 428a-c respectively comprised within a channel 408h-j. For example, information may be transferred inductively between electromagnetic elements 426a-c (e.g., electrically conductive elements) of the rotating member 402 and corresponding electromagnetic elements 428a-c (e.g., electrically conductive elements) of the stator 404 as further described in U.S. patent application Ser. No. 13/435,442, entitled "Contactless Communication Signal Transfer" and assigned to Analogic Corporation, which is incorporated herein by reference. As another example, the electromagnetic elements 426a-c of the rotating member 402 may respectively comprise an optical fiber and information may be transferred to the rotating member 402 from the stator 404 via light, emitted from one or more light emitting diodes (LEDs) positioned on the stator 404, for example, that travels through the optical fiber and is detected by a receiver positioned on the rotating member 402. Conversely, to transfer information from the rotating member 402 to the stator 404, the rotating member 402 may comprise one or more LEDs, for example, positioned within the one or more channels 408c-e and the stator 404 may comprise one or more optical fibers comprised within the channels 408h-j. Thus, the electromagnetic elements through which information is transferred may include, among other things, electrically conductive elements, optical fiber, and/or other communications mediums. For example, in another embodiment, radio frequency chips may be disposed in one of more of the channels 408c-e of the rotating member 402 and/or one or more of the channels 408h-j of the stator 404 to provide for information transfer between the rotating member 402 and the stator 404.

Respective pairs of elements (e.g., where a pair may be defined as an element of the stator 404 and a spatially proximate element of the rotating member 402), are typically configured to conduct information in a single direction (e.g., although respective pairs may be configured for bi-directional communications). As such, in order to conduct information bi-directionally, two pairs of elements may be utilized (e.g., with a first pair communicating information in a first direction and a second pair communicating information in a second direction). For example, a first pair of elements 426a, 428a may be configured to conduct information (e.g., such as communication information) from the stator 404 to components attached to the rotating member 402, and a second pair of elements 426b, 428b may be configured to conduct information (e.g., such as status information) from the rotating member 402 to the stator 404. In this illustrated embodiment, a third set of elements 426c, 428c may be further configured to supply additional and/or supplemental information between the rotating member 402 and the stator 404 (e.g., where more information is desired to be transmitted than is capable of being transmitted through a single pair of elements and/or where information is desired to be transmitted to two or more different components). For example, the third pair of elements 426c, 428c may be configured to provide command information (e.g., such as a gate signal) from the rotating member 402 to a power supply situated on the stationary side of the imaging modality whereas the second pair of elements 426b, 428c may be configured to provide status updates from the rotating member 402 to a user terminal (e.g., 126 in FIG. 1) on the stationary side of the imaging modality.

Typically, at least some of the elements 426a-c of the rotating member 402 that are configured to facilitate transferring information between the rotating member 402 and the stator 404 are on a same surface of the rotating member 402 as at least some of the elements 410, 418 of the rotating member 402 that are configured to facilitate transferring power between the rotating member 402 and the stator 404.

Figure 7:
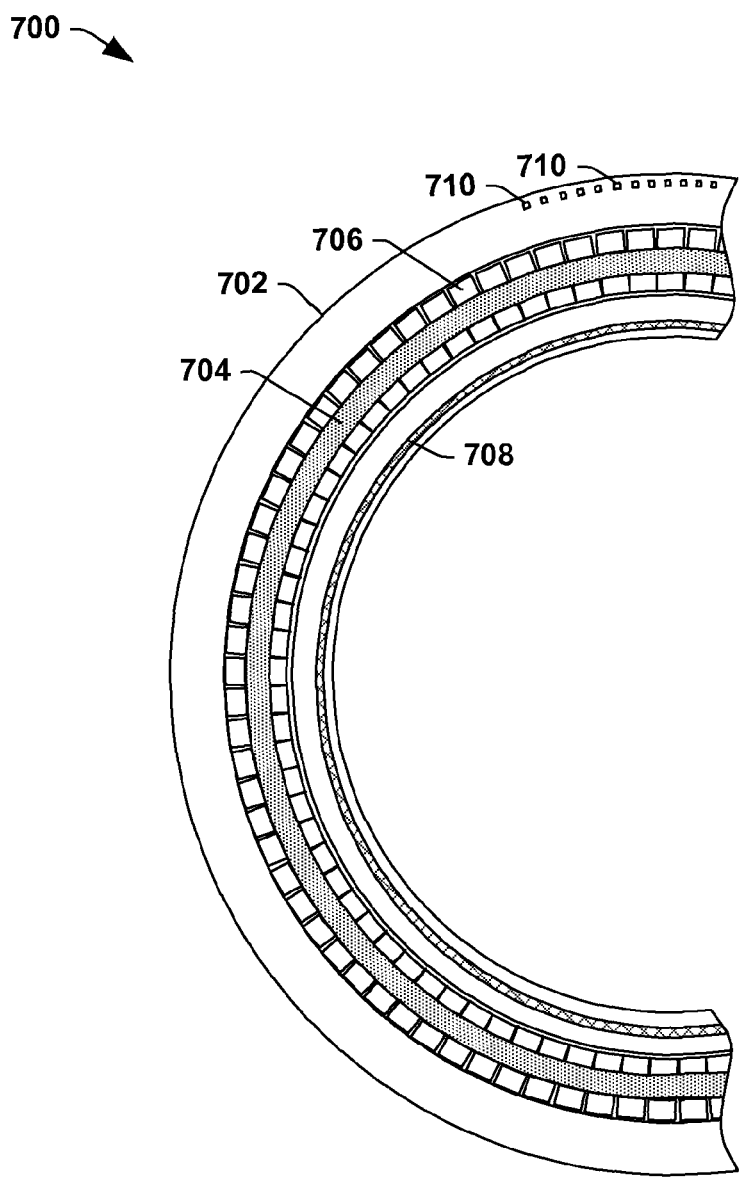
FIG. 7 illustrates an axial surface of a rotating member comprising elements to facilitate the transfer of power and/or information between the rotating member and a stator.

For example, in the illustrated embodiment, the elements 426a-c configured to facilitate transmitting information and the elements 410, 418 configured to facilitate transferring power are on an axial surface of the rotating member 402. Although, as illustrated in FIG. 7, at least some of the elements 410, 418,426a-c may be on a radial surface (e.g., 208 in FIG. 2) of the rotating member 402.

To facilitate the transfer of image data to the stator 404 from the rotating member 402, the rotating member 402 may also comprise a transmitting antenna assembly 430 and the stator 404 may comprise a receiving antenna 432. Typically, such a transmitting antenna assembly 430 is configured for transfer speeds that range between 500 megahertz and several gigahertz, although transfer speeds outside of this range are also contemplated. For example, U.S. patent application Ser. No. 13/453,203, entitled "Contactless Communication Signal Transfer" and assigned to Analogic Corporation, describes a wide-frequency bandwidth antenna assembly configured to transfer image data produced by a detector array to a receiver on the stationary side of an imaging modality and is incorporated herein by reference. As another example, U.S. Pat. No. 5,557,026, entitled "Apparatus for transferring data to and from a moving device" and assigned to Analogic Corporation, describes an antenna assembly for transferring image data between a moving device and a stationary device and is incorporated herein by reference.

As illustrated, the transmitting antenna assembly 430 is positioned on a different surface of the rotating member than the elements described above for facilitating the transfer of power and/or information. That is, the elements are positioned on the axial surface and the transmitting antenna assembly 430 is positioned on the radial surface. However, in another embodiment, at least some of the elements may be positioned on a same surface as the transmitting antenna assembly 430. Moreover, while FIG. 4 illustrates the transmitting antenna assembly as protruding from a surface of the rotating member 402, in another embodiment, the rotating member 402 may comprise a channel and the transmitting antenna assembly 430 may be positioned within the channel (e.g., to improve alignment of the transmitting antenna assembly 430 relative to the rotating member 402).

To facilitate ascertaining a rotation angle of the rotating member 402 (e.g., relative to a zero-degree reference) during the rotation of the rotating member 402, the rotating member 402 may further comprise one or more positioning elements 434 (e.g., slits, cavities, holes, notches, channels into which magnetic tape may be inserted, etc.) and the stator 404 may comprise a position component 436 configured to determine the rotation angle of the rotating member 402 based upon the one or more positioning elements. For example, in one embodiment, one or more notches 434 may be formed within the rotating member 402 and the positioning component 436 may be configured to emit a light beam, infrared beam, or other electromagnetic radiation 438 in the direction of the notches 434 to determine the rotation angle of the rotating member 402. Typically, the notches 434 are spaced evenly around the rotating member 402, and when the electromagnetic radiation 438 encounters a notch 434 (e.g., or when electromagnetic radiation is not reflected back to the position component 436), it may be determined that the rotating member 402 has rotated a predetermined distance. For example, in one embodiment, the rotating member 402 may comprise 360 notches spaced one-degree apart. As such, the position component 436 may determine that the rotating member 402 has rotated one-degree each time a beam of light, for example, emitted by the position component 436 encounters a notch 434 in the rotating member 402. In another embodiment, the positioning element formed within the rotating member 402 may comprise a channel into which magnetic tape or other strips of material may be inserted. The magnetic tape, for example, may be divided into magnetic and non-magnetic portions and the position component 436 may determine the rotation angle of the rotating member 402 based upon the number of magnetic portions that the position component 436 detects during the rotation (e.g., where magnetic portions may be spaced one-degree apart such that the detection of a magnetic portion indicates that the rotating member 402 has rotated another degree). As yet another example, the positioning element may comprise a channel into which a tic-fin (e.g., a thin sheet of metal or other material comprising one or more notches) is inserted.

The rotating member 402 may further comprise a drive channel 440 configured to receive a (substantially-annular) drive mechanism 442 (e.g., such a belt, rope, or other drive mechanism). Typically, the drive mechanism 442 is configured to rotate the rotating member 402 and is operatively coupled to the drive channel 440. That is, the rotating member 402 may be machined/manufactured with a channel 440 into which a drive mechanism 442, such as a belt, may be placed for rotating the rotating member 402. By way of example, as described with respect to FIG. 1, a rotator (e.g., 116 in FIG. 1) may be positioned on a stationary side of the imaging modality and the drive mechanism 442 may be coupled to the rotator to cause the rotating member 402 to rotate.

It may be appreciated that a belt is merely one example of a drive mechanism, and that other drive mechanisms are also contemplated. For example, the rotating member 402 may be machined/manufactured with one or more teeth that serve as the drive mechanism 442 and are configured to contact or engage with teeth of a rotator. As such, the rotating member 402 may not comprise a drive channel 440 because the drive mechanism 442 may be manufactured/machined to extend beyond a surface of the rotating member 402, for example.

In one embodiment, the rotating member 402 may be further machined or manufactured to comprise a bearing structure 444 (e.g., also referred to as a bearing surface or bearing face), that when coupled with a bearing structure 446 of the stator 404, for example, forms an assembled bearing, such as a ball bearing and/or an air bearing, configured to support at least some of the weight of the rotating member 402.

To ground the rotating member and/or reduce static charge in the rotating member 402, the stator 404 may further comprise a static discharge component 448, such as one or more metal brushes configured to contact the rotating member 402 and the rotating member 402 may be configured to physically contact the one or more brushes. For example, in one embodiment, the rotating member 402 may comprise a metal surface to which the one or more metal brushes are intended to make contact. Electrical charge created by the rotating member 402 may be transmitted to the stator 404 (e.g., and grounded) via the static discharge component 448. It may be appreciated that although FIG. 4 and subsequent figures illustrate the brushes as coming into physical contact with the rotating member 402, in another embodiment, the stator 404 may instead be in physical contact with the brushes. For example, the rotating member 402 may comprise a static discharge arm to which brushes are connected and the brushes may come into contact with the stator 404. In another embodiment, both the rotating member 402 and the stator 404 may both be in physical contact with brushes to ground the rotating member 402 and/or to reduce static charge in the rotating member 402, for example.

It may be appreciated that the arrangement of elements and/or components described with respect to FIG. 4 merely illustrates one example arrangement and is not intended to be interpreted as limiting the scope of the application, including the scope of the claims. That is, other arrangements for arranging the foregoing features of a rotating member are also contemplated. For example, FIG. 5 illustrates another example arrangement 500 where the rotating member 402 and the stator 404 are separated via a planar airgap 406 (e.g., as also illustrated in FIG. 3). In this example arrangement, the elements 410, 414 that are configured to facilitate high voltage power transfer are separated from the elements 418, 422 configured to facilitate lower voltage power transfer by elements 426*a-c*, 428*a-c* that are configured to facilitate information transfer. In yet another embodiment, some elements configured to facilitate information transfer may be separated from other elements configured to facilitate information transfer by elements configured to facilitate power transfer (e.g., to mitigate cross-talk). Moreover, it may be appreciated that some elements may be disposed on a different surface than other elements. For example, elements 426*c* and 428*c* (e.g., configured to facilitate the transfer of gate-drive information) may be positioned approximate the bearing structures 444, 446 (e.g., positioned on a radial surface) as opposed to on an axial surface as illustrated in FIGS. 4-5.

Figure 5:
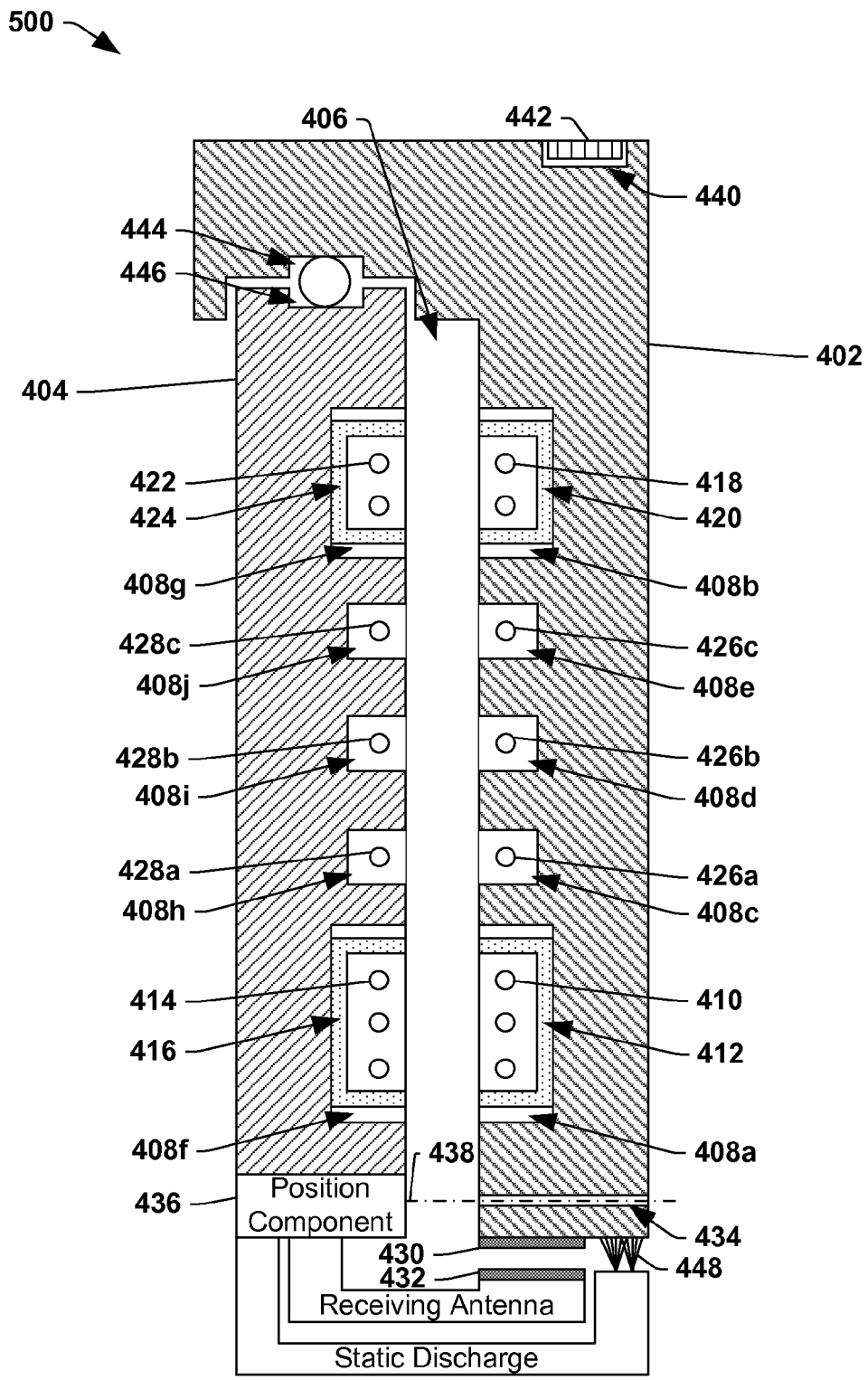
FIG. 5 illustrates a cross-sectional view of an example rotating member and a stator comprising elements to facilitate the transfer of power and/or information between the rotating member and the stator.
Figure 6:
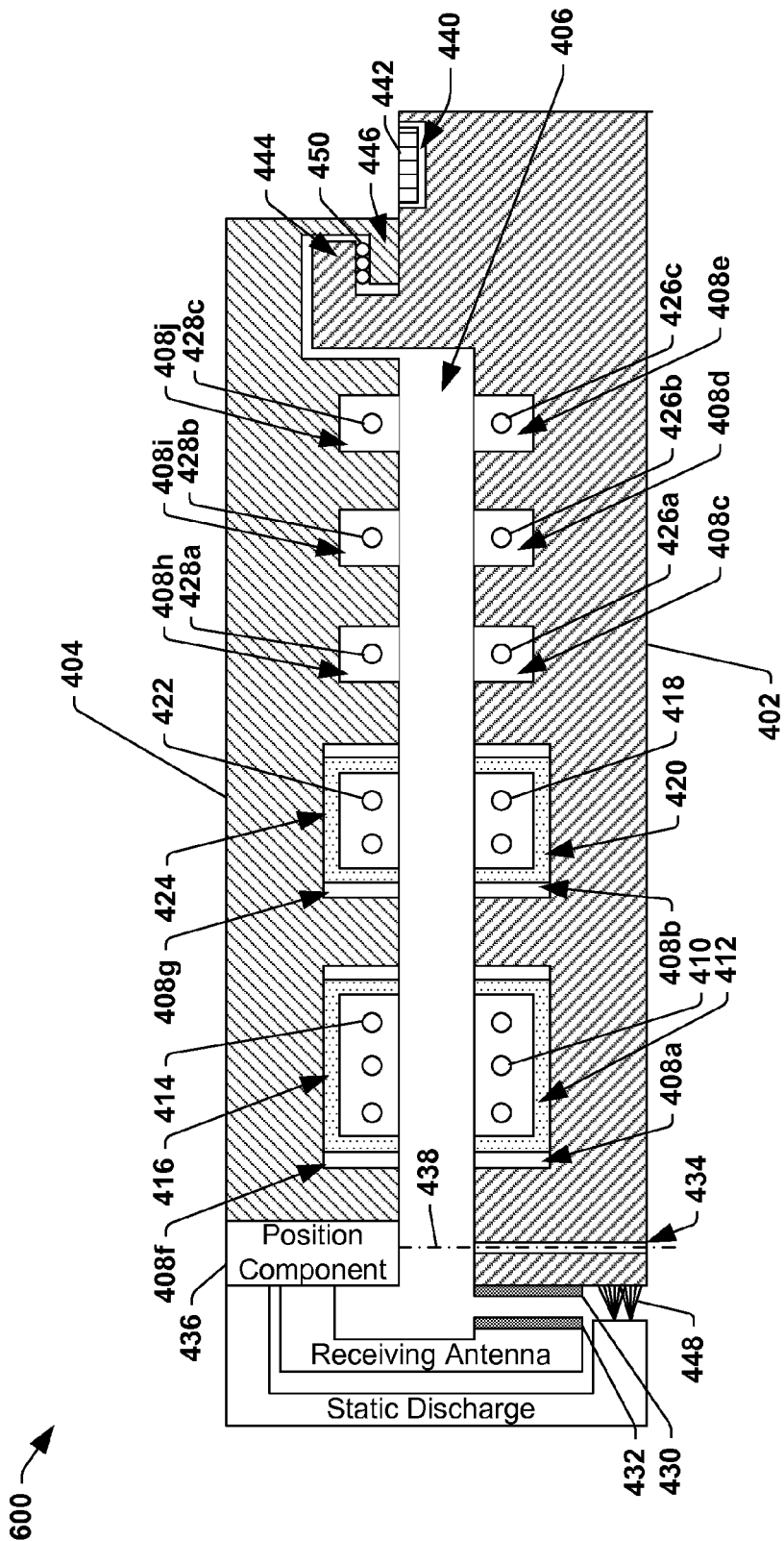
FIG. 6 illustrates a cross-sectional view of an example rotating member and a stator comprising elements to facilitate the transfer of power and/or information between the rotating member and the stator.

FIG. 6 illustrates yet another example arrangement of the elements and/or components described with respect to FIG. 4 when the airgap 406 is a cylindrical airgap (e.g., as shown in FIG. 2) as opposed to a planar airgap (e.g., as shown in FIGS. 3-5). That is, stated differently, illustrates a cross-sectional view (e.g., taken along line 6-6 in FIG. 2) of an example rotating member 402 (e.g., 202 in FIG. 2) and a stator 404 (e.g., 204 in FIG. 2) separated by an airgap 406 (e.g., 206 in FIG. 2). In such an embodiment, the elements 410, 418, 426*a-c* of the rotating member 402 may be disposed on a radial surface (e.g., 208 in FIG. 2) of the rotating member 402 and the elements 414, 422, 428*a-c* of the stator 404 may be disposed on a radial surface (e.g., 210 in FIG. 2) of the stator 404.

While the arrangement of the elements and components are substantially similar to the components illustrated in FIG. 4 (except that the elements/components are disposed on opposite surfaces), it may be appreciated that the bearing structure 444 of the rotating member 402 and/or the bearing structure 446 of the stator 404 may be slightly different given the difference in the orientation of the airgap 406. For example, in the illustrated embodiment, the bearing structure 444 of the rotating member 402 forms an (upside down) "L" shape that overlaps an (backwards) "L" shaped bearing structure 446 of the stator 404 (e.g., causing the bearing structures 444, 446 to lock together), and ball bearings 450, for example, may be positioned between the "L" shaped bearing structure 444 and the "L" shaped bearing structure 446.

FIG. 7 illustrates an axial surface 700 (e.g., 308 in FIG. 3) of a rotating member 702 (e.g., 302 in FIG. 3) of an imaging modality comprising a planer airgap (e.g., 306 in FIG. 3). It may be appreciated that for purposes of brevity/clarity, merely some of the components and/or elements described with respect to FIGS. 4-6 are illustrated. For example, FIG. 7 does not illustrate a bearing structure for supporting the rotating member 702 and/or a transmitting antenna assembly for transmitting image data to a stator (e.g., 304 in FIG. 3).

As illustrated, the rotating member 702 comprises an electrically conductive first element 704 (e.g., 410 or 418 in FIG. 4) configured to facilitate (high voltage or lower voltage) power transfer between the rotating member 702 and a stator of the radiation image modality and a ferromagnetic material 706 (e.g., 412 or 420 in FIG. 4). It may be appreciated that the rotating member 702 typically comprises a channel and the first element 704 is typically comprised within the first channel. Moreover, the ferromagnetic material 706 typically extends on both sides of the first element 704 and underneath the first element 704 (e.g., within the channel).

The rotating member 702 also comprises an electromagnetic second element 708 (e.g., 426*a*, 426*b*, or 428*c* in FIG. 4) configured to facilitate information transfer between the rotating member and the stator. It may be appreciated that the rotating member 702 typically comprises a (second) channel and the second element 706 is typically comprised within the channel. Moreover, it is to be noted that, in some embodiments, little to no ferromagnetic material surrounds the second element 708. Although, a dielectric material, such as a polymer, may electrically isolate the second element 708 from the (metal) rotating member 702, for example.

The rotating member 702 further comprises notches 710 (e.g., 434 in FIG. 4) formed within the rotating member 702 and configured to facilitate ascertaining a rotation angle of the rotating member. That is, stated differently, one or more notches 710 may be machined/manufactured into the rotating member 702 at specified locations. Using such notches 710, a position component (e.g., 436 in FIG. 4) may be configured to determine the rotation angle of the rotating member 702. It may be appreciated that other positioning elements, as described with respective to FIG. 4, such as a channel formed within the rotating member 702 comprising tic-fins and/or magnetic tape, for example, are also contemplated for use in determining a rotation angle of the rotating member 702 in combination with using the notches 710 or as an alternative to the notches 710, for example.

It may be appreciated that although FIG. 7 illustrates notches as being merely in a portion or range of the perimeter of the rotating member 702, such notches 710 may extend along the entire axial surface of the rotating member 702 at predetermined locations. For example, in one embodiment, the rotating member 702 may comprise 360 notches 710, with respective notches representative of a one-degree rotation of the rotating member 702.

It may also be appreciated that while the example rotating member 702 illustrates merely one element 704 configured to facilitate power transfer and merely one element 708 configured to facilitate information transfer, as described with respect to FIGS. 4-6, the rotating member 702 may comprise a plurality of elements configured to facilitate power transfer and/or a plurality of elements configured to facilitate information transfer.

The words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form. Also, at least one of A and B or the like generally means A or B or both A and B.

Although the disclosure has been shown and described with respect to one or more implementations, equivalent alterations and modifications may occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A gantry of a radiation imaging modality, comprising:
   a rotating member defining a first channel and a second channel, the first channel and the second channel disposed on a same surface of the rotating member, the second channel defined by a bottom surface and at least two sidewalls of the rotating member;
   an electrically conductive first element configured to facilitate power transfer between the gantry and a stator of the radiation imaging modality, the electrically conductive first element disposed within the first channel;
   a magnetic material disposed between the electrically conductive first element and a surface of the rotating member defining the first channel;
   an electromagnetic second element configured to facilitate information transfer between the gantry and the stator, the electromagnetic second element disposed within the second channel; and
   a non-conductive polymer, different than the magnetic material, disposed between the bottom surface and the electromagnetic second element and disposed between the at least two sidewalls and the electromagnetic second element, the non-conductive polymer electrically isolating the electromagnetic second element from the rotating member and the non-conductive polymer in contact with the rotating member and in contact with the electromagnetic second element.

2. The gantry of claim 1, the first channel and the second channel disposed on an axial surface of the rotating member.

3. The gantry of claim 1, comprising a transmitting antenna for transmitting image data between the gantry and the stator.

4. The gantry of claim 3, the first channel and the second channel disposed on a first surface of the rotating member and the transmitting antenna disposed on a second surface of the rotating member, the first surface perpendicular to the second surface.

5. The gantry of claim 4, the rotating member defining a third channel disposed on a third surface of the rotating member diametrically opposite the second channel and the gantry comprising a drive mechanism disposed within the third channel.

6. The gantry of claim 1, wherein:
   the electrically conductive first element is configured to facilitate power transfer at a high voltage,
   the rotating member defines a third channel disposed on the same surface of the rotating member as the first channel and second channel, and
   the gantry comprises:
      an electrically conductive third element configured to facilitate power transfer at a second voltage lower than the high voltage, the electrically conductive third element comprised within the third channel; and
      a second magnetic material disposed between the electrically conductive third element and a surface of the rotating member defining the third channel.

7. The gantry of claim 4, the second surface defining a static discharge region in which brushes, connected to the stator, contact the rotating member.

8. The gantry of claim 1, comprising:
   a drive channel; and
   a drive mechanism for rotating the rotating member, the drive mechanism operatively coupled to the drive channel.

9. The gantry of claim 1, comprising:
   a positioning element configured to emit a light beam towards the rotating member, wherein:
      the rotating member comprises a set of notches extending through the rotating member from a first surface facing the stator to a second surface diametrically opposite the first surface, and
      the set of notches are disposed at axial locations where the light beam intersects the rotating member.

10. The gantry of claim 1, comprising a first bearing structure for coupling the rotating member to a second bearing structure of the stator, the first bearing structure configured to facilitate rotation of the rotating member.

11. The gantry of claim 1, wherein the rotating member is configured to physically connect to at least one of a radiation source or a detector array.

12. The gantry of claim 1, the radiation imaging modality comprising a computed tomography (CT) imaging modality.

13. A computed tomography (CT) imaging modality, comprising:
   a rotating member defining a first channel, a second channel, and a third channel, the third channel defined by a bottom surface and at least two sidewalls of the rotating member;
   a first power transfer element configured to facilitate high voltage power transfer between the rotating member and a stator, comprising:
      an electrically conductive first element disposed within the first channel; and a first magnetic core disposed between the electrically conductive first element and a surface of the rotating member defining the first channel;

a second power transfer element configured to facilitate lower voltage power transfer between the rotating member and the stator, comprising:
an electrically conductive second element disposed within the second channel; and
a second magnetic core disposed between the electrically conductive second element and a surface of the rotating member defining the second channel; and a first communication element configured to facilitate information transfer between the rotating member and the stator, comprising:
an electromagnetic third element disposed within the third channel; and
a non-conductive polymer disposed between the bottom surface and the electromagnetic third element and disposed between the at least two sidewalls and the electromagnetic third element, the non-conductive polymer electrically isolating the electromagnetic third element from the rotating member.

14. The CT imaging modality of claim 13, wherein the rotating member is non-magnetic.

15. A gantry of a radiation imaging modality, comprising:
a rotating member defining a first channel and a second channel, the rotating member being non-magnetic, the second channel defined by a bottom surface and at least two sidewalls of the rotating member;
an electrically conductive first element configured to facilitate power transfer between the gantry and a stator of the radiation imaging modality, the electrically conductive first element disposed within the first channel;
a magnetic material disposed between the electrically conductive first element and a surface of the rotating member defining the first channel;
an electromagnetic second element configured to facilitate information transfer between the gantry and the stator, the electromagnetic second element disposed within the second channel; and
a non-conductive polymer, different than the magnetic material, disposed between the bottom surface and the electromagnetic second element and disposed between the at least two sidewalls and the electromagnetic second element, the non-conductive polymer electrically isolating the electromagnetic second element from the rotating member and the non-conductive polymer in contact with the rotating member and in contact with the electromagnetic second element.

16. The gantry of claim 15, wherein the rotating member comprises aluminum.

17. The gantry of claim 15, wherein the first channel and the second channel are disposed on a same surface of the rotating member.

18. The gantry of claim 15, wherein:
the rotating member defines a third channel, and
the gantry comprises:
an electrically conductive third element configured to facilitate power transfer between the gantry and the stator, the electrically conductive third element comprised within the third channel; and
a second magnetic material disposed between the electrically conductive third element and a surface of the rotating member defining the third channel.

19. The gantry of claim 18, wherein the electromagnetic second element is disposed between the electrically conductive first element and the electrically conductive third element.

20. The gantry of claim 18, wherein the electrically conductive first element facilitates a transfer of power having a first voltage and the electrically conductive third element facilitates transfer of power having a second voltage different than the first voltage.

* * * * *